United States Patent [19]

Li

[11] 4,018,712

[45] Apr. 19, 1977

[54] OXIDATION/AMMOXIDATION CATALYST

[75] Inventor: Tao P. Li, Chesterfield, Mo.

[73] Assignee: Monsanto Company, St. Louis, Mo.

[22] Filed: May 19, 1975

[21] Appl. No.: 578,586

Related U.S. Application Data

[63] Continuation-in-part of Ser. No. 429,010, Dec. 27, 1973, abandoned.

[52] U.S. Cl. ............................... 252/456; 252/458; 260/465.3
[51] Int. Cl.$^2$ ................... B01J 29/16; B01J 29/26; B01J 29/00
[58] Field of Search ........................... 252/456, 458; 260/465.3

[56] References Cited

UNITED STATES PATENTS

| | | | |
|---|---|---|---|
| 3,542,842 | 11/1970 | Grasselli et al. | 252/456 X |
| 3,551,470 | 12/1970 | Shaw et al. | 252/456 X |
| 3,925,255 | 1/1973 | Li et al. | 252/456 |

*Primary Examiner*—Carl F. Dees
*Attorney, Agent, or Firm*—J. C. Logomasini; P. L. Passley; N. E. Willis

[57] ABSTRACT

An oxidation/ammoxidation catalyst contains the elements antimony, uranium, iron, bismuth, and molybdenum, and optionally, nickel and/or cobalt, in a catalytic active oxidized state.

9 Claims, No Drawings

OXIDATION/AMMOXIDATION CATALYST

BACKGROUND OF THE INVENTION

This application is a continuation-in-part of copending application Ser. No. 429,010 filed Dec. 27, 1973, now abandoned.

This invention relates to an improved oxidation and/or ammoxidation catalyst system containing the elements antimony, uranium, iron, bismuth and molybdenum, and optionally, nickel or cobalt, and to a method for preparing such catalyst system.

It is well known that olefins can be oxidized to oxygenated hydrocarbons such as unsaturated aldehydes and acids, for example, acrolein and methacrolein, and acrylic and methacrylic acid. It is also well known that olefins can be ammoxidized to unsaturated nitriles such as acrylonitrile and methacrylonitrile. The value of such oxygenated hydrocarbons and unsaturated nitriles is generally well recognized with acrylonitrile being among the most valuable monomers available to the polymer industry for producing useful polymeric products.

Various catalytic processes are known for the oxidation and/or ammoxidation of olefins. Such processes commonly react an olefin or an olefin-ammonia mixture with oxygen in the vapor phase in the presence of a catalyst. For the production of acrolein and acrylonitrile, propylene is the generally used olefin reactant and for the production of methacrolein and methacrylonitrile, isobutylene is the generally used olefin reactant.

A catalyst system composed of the oxides of antimony and uranium and the oxidation and the ammoxidation of olefins using such catalyst has been described in U.S Pat. Nos. 3,198,750 and 3,308,151. These patents describe preparation of the catalyst by precipitation wherein the oxides of the elements are contained in a slurry which is filtered to remove soluble salts and recover the catalytic components as the filter cake. U.S. Pat. No. 3,328,315 further describes modification of an antimony-uranium containing base catalyst with additional elements including iron and bismuth. U.S. Pat. No. 3,542,842 describes oxidation catalysts containing oxides of uranium and molybdenum in combination with at least one additional element including bismuth, cobalt, iron and nickel. U.S. Pat. No. 3,551,470 describes oxidation catalysts containing oxides of antimony, uranium and molybdenum and, optionally, iron. These two patents illustrate two different types of catalyst. In U.S. Pat. No. 3,551,470 the principal components are antimony and uranium and minor amounts of molybdenum and iron (optionally) are introduced to modify the activity of this basic composition. U.S. Pat. No.3,542,842 on the other hand discloses a catalyst that has as its principal components molybdenum and uranium with a minor amount of one or more of a number of modifying elements. These two patents represent two quite different approaches to the problems of defining a catalyst composition for oxidation and ammoxidation processes. As may be seen from a comparison of the results reported in the Examples in the two patents, the catalyst composition of U.S. Pat. No. 3,551,470 is much superior in performance.

The catalyst of the present invention is a further modification of this more effective type of catalyst, (that is, one based on antimony and uranium), by a further modification of the catalyst composition that leads to a surprising degree of improvement especially when the catalyst composition is prepared in a particular manner.

In copending application Ser. No. 320,373, filed Jan. 2, 1973 U.S. Pat. No. 3,925,255, a catalyst system based on the elements antimony, uranium, bismuth and iron prepared by a novel procedure is described and claimed. This catalyst is shown to be useful for producing acrylonitrile from propylene.

In the catalytic oxidation and/or ammoxidation of olefins, the commercial utility of a catalyst system is highly dependent upon the cost of the system, the conversion of the olefin and the yield of the desired product and the stability of the catalyst during operation. In many cases a reduction in the cost of a catalyst system in the order of a few pennies per pound or a 1% increase in the yield of a desired product and/or an improvement in the stability of the catalyst represents a tremendous commercial economical savings. Accordingly, research efforts are continuously being made to define new or improved catalyst systems and methods of making new and old catalyst systems to reduce the cost and/or to upgrade the activity, selectivity and stability of such catalyst systems in particular processes.

SUMMARY

This invention is directed to an improved catalyst system containing the elements antimony, uranium, iron, bismuth and molybdenum, and optionally, nickel or cobalt having activity, selectivity and stability useful for commercial catalytic oxidation and/or ammoxidation of olefins and to an improved method of making such catalyst system.

The term "stability" as used herein is intented to mean the ability of the catalyst system to maintain its activity and selectivity for the desired products during the desired reaction, i.e., under a reducing atmosphere and/or adverse conditions for maintaining its oxidized state.

Accordingly, typical objects of this invention are to provide: (1) an improved oxidation and/or ammoxidation catalyst system containing oxygen, antimony, uranium, iron, bismuth and molybdenum, and optionally, nickel or cobalt, (2) an improved process for the preparation of a catalyst system containing oxygen, antimony, uranium, iron, bismuth and molybdenum, and optionally, nickel or cobalt, and (3) an improved olefin conversion process.

Other objects, aspects and advantages of this invention will become apparent to those skilled in the art upon further study of this disclosure and the appended claims.

In accordance with this invention, a new oxidation/ammoxidation catalyst system based on the elements antimony, uranium, iron, bismuth and molybdenum, and optionally, nickel or cobalt is provided. The elements are in the catalyst in combination with oxygen and may exist therein individually as oxides, as oxygen complexes (a single complex of all the elements or group of complexes having all the elements present with each complex containing two or more of the elements) or as a combination of said oxides and said complexes. The atomic ratio of the elements present in the catalyst system may vary over a wide range. Generally speaking the catalyst may be defined by the following empirical formula:

$$Sb_aU_bFe_cBi_dMo_eMe_fO_g$$

wherein Me is nickel or cobalt, $a$ is 1 – 10, $b$ is 0.1 to 5, $c$ is 0.1 to 5, $d$ is 0.001, $e$ is 0.001 to 0.1, $f$ is 0 to 0.1 and $g$ is a number taken to satisfy the valences of the quantities of Sb, U, Fe, Bi and Mo, including Ni and Co if present, in the oxidation states in which they exist in the catalyst and generally is 3.6 to 48.2.

The catalyst can be prepared by any known method and generally one will start with individual oxides or salts of the elements. One convenient method of preparing the catalyst is to first combine the oxides or sulfates of antimony, uranium, iron and bismuth with sulfuric acid. When antimony sulfate is used as a starting material, it can be added to water wherein sulfuric acid is obtained. Nitric acid is used to oxidize the sulfate salts of the elements or to further oxidize the oxides of the elements. After the acid mixture has digested, the pH of the mixture is adjusted to about 8 causing precipitation and then filtered.

After filtering the mixture, the filter cake can be dried at a temperature of from about 100° to about 180° C. A catalyst support may be added prior to drying. A suitable drying temperature is about 110° C. However, the drying can be obtained at higher temperatures such as up to about 650° C. The time required for drying the filter cake can range from an hour up to about 64 hours. Obviously, the drying temperature selected will dictate the required drying time with the lower temperatures requiring the longer time. Also, the filter cake may be dried at different temperatures, for example at 110° C for from 2 to 64 hours and then at a temperature of from about 250° to about 650° C for from 2 to 24 hours. Drying of the catalyst can be advantageously accomplished by spray drying.

After the filter cake is dried, it is further heated at an elevated temperature to obtain the active catalytic form of the elements. This calcination of the catalyst is conducted at a temperature in the range of from about 500° to about 1150° C. The time for calcination can vary and depends upon the temperatures employed. Generally, a time period of 1 to 24 hours at the designated temperatures is sufficient. The calcination may be conducted in the presence of oxygen (air); however, the catalyst may also be made active by calcining it in the absence of oxygen, such as in a nitrogen atmosphere.

The molybdenum component of the catalyst can be added initially by mixing with the precipitates of the other elements or it can be added by impregnation of a prepared catalyst, containing the other disclosed elements, as further described herein in Example I. The molybdenum component can be added as an oxide or as a salt of molybdenum, such as nickel molybdate, cobalt molybdate, bismuth molybdate, ferric molybdate or ammonium molybdate. The activity and stability of the catalyst is not adversely affected by the presence of nickel or cobalt and exhibits improvement when bismuth or ferric molybdates are present.

The catalyst can be employed without support, and will display excellent activity. It also can be combined with a support, and preferably at least 5% up to about 90% preferably 5 to 50%, of the supporting compound by weight of the entire composition is employed in this event. Any known support materials can be used, such as, for example, silica, alumina, zirconia, alundum, silicon carbide, aluminasilica, and the inorganic phosphates, silicates, aluminates, borates and carbonates stable under the reaction conditions to be encountered in the use of the catalyst.

The improved catalyst of this invention exhibits exceptional utility in the conversion of olefins with or without the presence of ammonia. The olefins employed as reactants for conversion by the catalyst of this invention may be open chain as well as cyclic and include, for example, propylene, butene-1, butene-2, isobutene, pentene-1, pentene-2, 3-methyl butene-1, 2-methyl butene-2, hexene-1, hexene-2, 4-methyl pentene-1, 3,3 dimethylbutene-1, 4-methyl pentene-2, octene-1, cyclopentene, cyclohexene, and the like. Particularly, when the catalyst of this invention is used as merely an oxidation catalyst, it is particularly adapted to the conversion of propylene to acrolein and isobutylene to methacrolein. Of course, mixtures of olefins may be employed and mixtures of olefins with other hydrocarbons are applicable to the process of this invention. When the catalyst of this invention is to be used as an ammoxidation catalyst, the olefins as aforestated are applicable. However, the catalyst of this invention is particularly adapted to the conversion of propylene with ammonia and oxygen to acrylonitrile at 250° to 650° C.

The molar ratio of oxygen to the olefin in the feed will generally be in the range of 0.5:1 to 4:1 with a preferred ratio being 1:1 to 3:1. The molar ratio of ammonia to olefin in the feed will generally be in the range of 0.5:1 to 5:1 and preferably slightly over the stoichiometric ratio of 1:1 ammonia:olefin will be employed.

While ammonia is most generally employed as the nitrogen providing compound, other nitrogen containing materials may be employed which decompose to produce reactive nitrogen under the reaction conditions. Any source of oxygen, pure or in admixture with inerts, may be employed in the process of this invention. Air is a satisfactory source of oxygen for use in this invention.

The catalyst system of this invention can be advantageously employed for synthesizing styrene from ethylbenzene and oxygen, butadiene from butenes and oxygen, acrolein or methacrolein from propylene or isobutylene and oxygen, acrylonitrile or methacrylonitrile from propylene or isobutylene, ammonia and oxygen, isoprene from 2-methyl butene-2 and oxygen, and 2-cyano-1, 3-butadiene from 2-methyl butene-2 or isoprene, ammonia and oxygen.

DESCRIPTION OF PREFERRED EMBODIMENTS

The following Examples are presented as illustrative of the invention and, as such, are not intended to be restrictive upon the specific materials, quantities and operation variables specifically set forth therein.

As used in the examples, the following terms have the following definitions:

% propylene ($C_3H_6$) converted =

$$\frac{\text{mols } C_3H_6 \text{ in feed} - \text{mols } C_3H_6 \text{ in effluent}}{\text{mols } C_3H_6 \text{ in feed}} \times 100$$

$$\% \text{ propylene to acrylonitrile} = \frac{\text{mols AN formed}}{\text{mols } C_3H_6 \text{ in feed}} \times 100$$

In the examples either reactor A or reactor B is employed in carrying out the particular runs. Reactor A consists of a 25 mm outside diameter 96% quartz tube having a volume of about 120 ml and fitted at the top with a fritted disc to remove entrained catalyst from the effluent and at the bottom with a feed sparger. A thermowell of 6 mm outside diameter 96% quartz glass extends through the center of the catalyst bed to the bottom of the reactor. The reactor tube is jacketed with a larger tube in which sand is fluidized for providing even heat distribution. Reactor B consists of a 3.175 inch inside diameter stainless steel tube 36 inches long fitted at the bottom with a feed sparger consisting of six ⅛-inch outside diameter tubes connected to a feed entry line and fitted at the top with a flanged closure member. Within the reaction is a dual cyclone system having 1 inch cyclone bodies and ½-inch diplegs. The product outlet extends from the upper cyclone through the top closure member. A plurality of 4 mesh screens at 3 inch spacings are positioned in the lower two-thirds of the reactor. A thermowell of ½-inch outside diameter tubing extends through the catalyst bed. The reactor tube is jacketed with a larger tube in which sand is fluidized for providing even heat distribution. The reactors A and B are placed in controlled, hinged tube furnaces. The reactant gases are premixed and heated to about 420° C. before entering the bottom of the reactor through the sparger system. The effluent gases from the reactor are heated to prevent condensation prior to chromatographic analysis.

EXAMPLE I

A catalyst system composed of antimony, uranium, iron and bismuth is prepared by adding 784.2 gms. $Sb_2O_3$, 269.4 gms. $U_3O_8$, 13.55 gms. $Bi_2O_3$ and 533.6 gms. $FeSo_4 \cdot 7H_2O$ to 4200 ml. of water to which is then added 1193 grams of 98% $H_2SO_4$. The mixture is stirred for about 3 hours at a temperature of 94° C. 82.8 gms. of 70% nitric acid is added to the mixture which is then stirred for 1 hour to further oxidize the elements. After cooling the mixture the pH is adjusted to about 8 with 58% ammonium hydroxide diluted with 3 parts water. After precipitation occurs the slurry is vacuum filtered and the precipitate is washed with 16 liters of water. The precipitate is reslurried with 1200 ml. of water and mixed with 2333 gms. of silica sol (30% $SiO_2$) and the slurry is heated until a viscosity suitable for spray drying is obtained. The slurry is then spray dried at a temperature of about 150° C. The dried catalyst is calcined at 900° C for 1 hour in a fluidized state in the presence of oxygen. The catalyst has a nominal formula of $Sb_{1.85}U_{0.33}Fe_{0.66}Bi_{0.02}$ - 35% $SiO_2$. One thousand grams of the dried catalyst after calcination is impregnated with a mixture of 5.086 gms. $(NH_4)_6Mo_7O_{24} \cdot 4H_2O$ and 785 ml. water per 1000 gms. of catalyst. This impregnated catalyst is dried in an oven at 110° C for about 16 hours and then recalcined at 550° C for 2 hours in the presence of oxygen. This calcined portion of the catalyst has a nominal formula of $Sb_{1.85}U_{0.33}$ - $Fe_{0.66}Bi_{0.02}Mo_{0.02}$ - 35% $SiO_2$.

EXAMPLE II

The molybdenum modified and unmodified catalyst systems made according to Example I are used in the conversion of propylene and ammonia to acrylonitrile using Reactor A. The feed composition in these comparative runs is 8.9% ammonia, 8.5% propylene, 17.3% oxygen and 65.3% helium. In each run the temperature is about 465° C and the pressure is 2.25 kg/cm². The feed rate in each run is such that the propylene loading is 0.115 kg/kg catalyst/hour. The results are given in Table I.

TABLE I

| Catalyst | Unmodified | Mo Modified |
| --- | --- | --- |
| Percent Propylene Converted | 97.6 | 97.3 |
| Percent Propylene to Acrylonitrile | 69.9 | 72.4 |
| Stability S- Stable U- Unstable | U | S |

The above example shows the improved ammoxidation activity, the improved stability and the improvement of acrylonitrile yield of the molybdenum modified catalyst system of this invention compared with the unmodified catalyst under pressure operation.

EXAMPLE III

The molybdenum modified catalyst system made according to Example I is used in the conversion of propylene and ammonia to acrylonitrile under a pressure of 2.25 kg/cm² using Reactor B previously described. The feed composition charged to the reactor has a ratio of 9.7 air:1 propylene:1.05 ammonia. The reactor is charged initially with 2000 gms of the catalyst and the feed rate is 24 liters/minute (STP). Due to catalyst loss the contact time* for sample B is 2.85 compared to 5.4 for sample A and the propylene and loading for sample B is 0.19 kg/kg catalyst/hour compared to 0.1 for sample A. Other process data and the results are given in Table II.

TABLE II

| Sample | A | B |
| --- | --- | --- |
| Elapsed Reaction Time (Hours) | 1 | 164 |
| Reactor Temperature (° C) | 456 | 449 |
| Percent Propylene Converted | 97.7 | 97.8 |
| Percent Propylene to Acrylonitrile | 73.2 | 75.2 |

*Contact time determined as $\frac{\text{Weight of Catalyst (grams)}}{\text{Feed Flow Rate (ml/sec.) at STP}}$ The above example shows that the Mo modified catalyst is effective and stable over an extended period of operation and at variable loadings of propylene.

EXAMPLE IV

The molybdenum modified catalyst system made according to Example I is used in the conversion of propylene and ammonia to acrylonitrile under a pressure of 2.25 kg/cm² using the Reactor B previously described. The feed composition charged to the reactor containing 1500 grams of catalyst has a ratio of 9.77 air:1 propylene:1 ammonia. The contact time* is 3.75 and the propylene loading is 0.153 kg/kg catalyst/hour. Other process data and the results are given in Table III.

TABLE III

| Sample | A | B | C | D |
| --- | --- | --- | --- | --- |
| Elapsed Reaction Time (Hours) | 1 | 23 | 51 | 75 |
| % Propylene Converted | 93.0 | 95.8 | 96.7 | 97.1 |
| % Propylene to Acryloni- | 75.0 | 76.0 | 75.7 | 75.5 |

TABLE III-continued

| Sample | A | B | C | D |
|---|---|---|---|---|
| trile | | | | |

*Contact time determined as $\frac{\text{Weight of Catalyst (grams)}}{\text{Feed Flow Rate (ml/sec.) at STP}}$ The above example shows that the Mo modified catalyst is effective and stable over an extended period of operation at a high level of propylene loading.

EXAMPLE V

Three catalysts are prepared by first preparing a base catalyst having a nominal formula of $Sb_{1.85}U_{0.33}Fe_{0.66}Bi_{0.02}$ - 35% $SiO_2$ in accordance with the procedure used in Example I to the point prior to spray drying:

A — 1000 grams of the base catalyst slurry is mixed with 5.086 grams of $(NH_4)_6Mo_7O_{24}\cdot 4H_2O$ dissolved in 100 grams of $H_2O$ and then spray dried. The catalyst has a nominal formula $Sb_{1.85}U_{0.33}Fe_{0.66}Bi_{0.02}Mo_{0.02}$ - 35% $SiO_2$. The spray dried catalyst is calcined at 850° C for 2 hours using an 8% oxygen atmosphere.

B — 666 grams of the base catalyst slurry is mixed with 4.544 grams of pulverized $CoMoO_4\cdot 4H_2O$ and then spray dried. The catalyst has a nominal formula of $Sb_{1.85}U_{0.33}Fe_{0.66}Bi_{0.02}$ - $Co_{0.02}Mo_{0.02}$ - 35% $SiO_2$. The spray dried catalyst is calcined at 850° C for 1 hour using an 8% oxygen atmosphere.

C — 666 grams of the base catalyst slurry is mixed with 6.823 grams of $CoMoO_4$ prepared by dissolving 8.375 grams of $Co(NO_3)_2\cdot 6H_2O$ in 50 ml of water, dissolving 4.142grams of $MoO_3$ in 40 ml of water to which is added 4.75 ml of concentrated $NH_4OH$ and then heated to evaporate excess $NH_3$ until the pH is 7, mixing the cobalt solution with the molybdenum solution and boiling the mixture for 1 hour to complete precipitation of $CoMoO_4$, and washing the precipitate with water and then suspending it in 100 ml of water. The catalyst slurry is spray dried and has a nominal formula of $Sb_{1.85}U_{0.33}$ - $Fe_{0.66}Bi_{0.02}Co_{0.03}Mo_{0.03}$ - 35% $SiO_2$. The spray dried catalyst is calcined at 850° C for 1 hour using an 8% oxygen atmosphere.

EXAMPLE VI

The catalysts of Example V are used in the conversion of propylene and ammonia to acrylonitrile using Reactor A. The feed composition used is 8.6% ammonia, 8.2% propylene, 16.6% oxygen and 66.6% helium. In each run the reactor contains 70 grams of catalyst and the contact time* is 5. Other reaction variables and the results are given in Table IV.

TABLE IV

| Catalyst | Ex.V-A | Ex.V-B | Ex.V-C | |
|---|---|---|---|---|
| Temp. ° C | 465 | 465 | 455 | 460 |
| Elapsed Reaction Time (hours) | | | 1 | 25 |
| % Propylene Converted | 97.7 | 97.9 | 96.6 | 97.1 |
| % Propylene to Acrylonitrile | 71.7 | 72.1 | 72.0 | 72.0 |

The above example shows that the Mo modified catalyst further modified with cobalt is effective and stable over an extended period of operation.

EXAMPLE VII

The Mo modified catalyst system of Example I is used in the conversion of isobutylene to methacrylonitrile using the apparatus previously described. Methacrylonitrile is obtained using each catalyst with a feed composition of 8.9% ammonia, 8.5% isobutylene, 17.5% oxygen and 65.1% helium, all on a volume basis, at a temperature of 500° C and atmospheric pressure.

EXAMPLE VIII

The Mo modified catalyst system of Example I is used in the conversion of propylene to acrolein using the apparatus previously described. Acrolein is obtained using each catalyst with a feed composition of 7.0% propylene, 11% oxygen and 82% helium, all on a volume basis, at a temperature of 500° C and atmospheric pressure.

EXAMPLE IX

Acatalyst similar to that of Example V-B is made using nickel molybdate in place of the $CoMoO_4$. Propylene is converted to acrylonitrile in the presence of ammonia and oxygen with the nickel modified catalyst.

EXAMPLE X

A catalyst composition having the following composition;

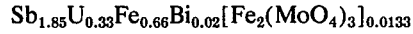

is prepared in the manner described below.

The following are added to 6300 ml of water with stirring to obtain a uniform mixture:
1176.3 gm of antimony trioxide, $(Sb_2O_3)$
404 gm of uranium oxide, $(U_3O_8)$
800.4 gm of ferrous sulphate, $(FeSO_4\cdot 7H_2O)$
20.3 gm of bismuth trioxide $(Bi_2O_3)$ The mixture is then treated with 1789.5 gm of 98% sulphuric acid added slowly and with stirring and during the addition the mixture is observed to thicken. When the sulphuric acid addition has been completed the mixture is heated, with stirring for 3 hours at 94° C.

70% Nitric acid (124.2 gm) is then added slowly with stirring and the mixture is maintained at the same temperature for 1 hour after addition of the nitric acid is completed. Thereafter the solution is cooled and the pH is adjusted to 8 using 58% ammonium hydroxide diluted with 3 parts of water. This leads to precipitation. The mixture is covered and allowed to stand for 16 hours after which it is vacuum filtered and washed with water. The filter cake thus obtained is re-slurried in 2 liters of water.

3500 grams of a 30% silica sol are then added and the slurry is concentrated by evaporation. It is then divided into five equal portions.

A solution of 9.55 gm of ferric nitrate nonahydrate in 67 ml of water and a solution of 5.1 gm of molybdenum trioxide in 53 ml of water and 6 ml of 58% ammonium hydroxide (heated till pH 7 is attained) are prepared. The molybdate solution is added dropwise to the ferric nitrate solution causing precipitation of ferric molybdate. This precipitate is filtered and washed and slurried in water.

The ferric molybdate is then mixed with one portion of the slurry containing the antimony, uranium, iron, bismuth and silica and the mixture is heated until it attained a viscosity at which it could conveniently be spray-dried and then is sprayed-dried at about 150° C and calcined at 850° C for 1 hour in an 8% oxygen atmosphere to produce the finished catalyst.

EXAMPLE XI

Four catalysts are prepared using the other portions of the slurry prepared in Example X and according to the manner described in Example X except for the particular molybdate added. The particular molybdates added are identified in Column X in Table V.

EXAMPLE XII

The catalyst prepared by Examples X and XI having the nominal formula:

$$Sb_{1.85}U_{0.33}Fe_{0.66}Bi_{0.02}X_y - SiO_2\ 35\%$$

wherein X is the molybdate and y the atoms of molybdenum present are used in the conversion of propylene to acrylonitrile using Reactor A described above.

The feed to the reaction is 8.5 vol % propylene, 8.9 vol % ammonia, 17.3 vol % oxygen and 65.3 vol % helium. The pressure in the reactor is maintained at 1.16 kg/cm² and the contact time (as defined above) was 5.

The results are set forth in Table V below.

TABLE V

| X | y | Temp(° C) | Propylene Conversion | Propylene to Acrylonitrile |
|---|---|---|---|---|
| (NH$_4$)$_6$Mo$_7$O$_{24}$ | 0.02 | 465 | 96.2 | 71.1 |
| Co Mo O$_4$ | 0.03 | 465 | 97.0 | 71.8 |
| *Ni Mo O$_4$ | 0.02 | 470 | 95.2 | 69.3 |
| Bi$_2$(MoO$_4$)$_3$ | 0.01 | 455 | 97.1 | 71.6 |
| Fe$_2$(MoO$_4$)$_3$ | 0.04 | 450 | 96.6 | 73.9 |

*Catalyst calcined in 10% oxygen atmosphere for 1 hour at 900° C.

From the foregoing Examples it will be clearly noted that the catalyst system of this invention exhibits activity, selectivity and stability when used at elevated pressures. Also, it will be observed from the above Examples that the catalyst of this invention operates effectively under a high loading of reactant. The ability of the catalyst to catalyze a higher quantity of reactant per unit of time offers a considerable economic advantage over presently known ammoxidation catalysts. Commercially speaking, the catalyst of this invention permits manufacturing reactors to be designed smaller or for more product to be produced in existing reactors.

In addition, from the results set forth in Example XII, it can be seen that the addition of molybdenum as a molybdate of one of the other catalyst elements, particularly ferric molybdate, gives even more advantageous results.

It will be obvious to persons skilled in the art that various modifications may be made in the improved catalyst and process as described in this application. Accordingly, it is intended that all such modifications which reasonably fall within the scope of the appended claims are a part hereof.

What is claimed is:

1. A catalyst system suitable for operation under pressure comprising the elements antimony, uranium, iron, bismuth and molybdenum, and optionally nickel or cobalt, in an oxidized state represented by the nominal formula:

$$Sb_aU_bFe_cBi_dMo_eMe_fO_g$$

wherein Me is nickel or cobalt, a is 1 to 10, b is 0.1 to 5, c is 0.1 to 5, d is 0.001 to 0.1, e is 0.001 to 0.1, f is 0 to 0.1 and g is a number taken to satisfy the valences of the aquantities of Sb, U, Fe, Bi and Mo, including Ni and Co if present, in the oxidation states in which they exist in the catalyst.

2. The catalyst system of claim 1 carried on a support.

3. The catalyst composition of claim 1 prepared by forming a mixture of oxides or sulfates of antimony, uranium, bismuth and iron in sulfuric acid, digesting the resulting mixture, adjusting the pH to about 8, filtering the mixture, mixing the filter cake with silica sol, evaporating the filter cake mixture to dryness, calcining the mixture at 800° to 900° C, impregnating the calcined filter cake mixture with a molybdenum compound and then heating the dried mixture at a temperature of from about 500° to about 1150° C to form said active catalyst.

4. The catalyst composition of claim 3 wherein said mixture is formed from Sb$_2$O$_3$, U$_3$O$_8$, Bi$_2$O$_3$ and FeSO$_4$·7H$_2$O.

5. The catalyst composition of claim 3 wherein said molybdenum compound is (NH$_4$)$_6$Mo$_7$O$_{24}$·4H$_2$O.

6. The method of forming a catalyst composition having the nominal formula $$Sb_aU_bFe_cBi_dMo_eMe_fO_g$$

wherein Me is nickel or cobalt, a is 1 to 10, b is 0.1 to 5, c is 0.1 to 5, d is 0.001 to 0.1, e is 0.001 to 0.1, f is 0 to 0.1 and g is a number taken to satisfy the valences of the quantities of Sb, U, Fe, Bi and Mo, including Ni and Co if present, in the oxidation states in which they exist in the catalyst which comprises forming a mixture of oxides or sulfates of antimony, uranium, bismuth and iron in sulfuric acid, digesting the resulting mixture, adjusting the pH to about 8, filtering the mixture, mixing the filter cake with silica sol, mixing a molyobdenum compound with the filter cake - silica sol mixture and evaporating the molybdenum compound - containing mixture to dryness and then heating the dried mixture at a temperature of from about 500° to 1150° C to form the active catalyst.

7. The method of claim 6 wherein said molybdenum compound is cobalt molybdate.

8. The method of claim 6 wherein said molybdenum compound is bismuth molybdate.

9. The method of claim 6 wherein said molybdenum compound is ferric molybdate.

* * * * *

UNITED STATES PATENT OFFICE
CERTIFICATE OF CORRECTION

PATENT NO. : 4,018,712
DATED : April 19, 1977
INVENTOR(S) : Tao P. Li

It is certified that error appears in the above-identified patent and that said Letters Patent are hereby corrected as shown below:

At Column 3, line 4, "d is 0.001" should read
--d is 0.001 to 0.1--.

At Column 5, line 13, "reaction" should read
--reactor--.

At Column 5, line 18, "1/2-inch" should read
--1/4-inch--.

At Column 6, line 27, after "and the propylene" the word "and" should be deleted to read:

"and the propylene loading"

Signed and Sealed this

Twenty-eighth Day of June 1977

[SEAL]

Attest:

RUTH C. MASON
*Attesting Officer*

C. MARSHALL DANN
*Commissioner of Patents and Trademarks*